United States Patent [19]
Tomita et al.

[11] Patent Number: 5,804,555
[45] Date of Patent: *Sep. 8, 1998

[54] ANTIOXIDANT

[75] Inventors: Mamoru Tomita; Seiichi Shimamura, both of Kanagawa; Kouzo Kawase, Saitama; Yasuo Fukuwatari, Kanagawa; Mitsunori Takase, Saitama; Wayne Robert Bellamy, Kanagawa; Koji Yamauchi, Kanagawa; Hiroyuki Wakabayashi, Kanagawa; Yukiko Tokida, Kanagawa, all of Japan

[73] Assignee: Morinaga Milk Industry Co., Ltd., Tokyo, Japan

[ * ] Notice: The term of this patent shall not extend beyond the expiration date of Pat. No. 5,656,591.

[21] Appl. No.: 381,984

[22] PCT Filed: Aug. 4, 1993

[86] PCT No.: PCT/JP93/01090

§ 371 Date: Apr. 11, 1995

§ 102(e) Date: Apr. 11, 1995

[87] PCT Pub. No.: WO94/03555

PCT Pub. Date: Feb. 17, 1994

[30] Foreign Application Priority Data

Aug. 7, 1992 [JP] Japan .................................. 4-211335

[51] Int. Cl.$^6$ ............................ A61K 38/01; C07K 14/79
[52] U.S. Cl. .................................................. 514/12; 514/21
[58] Field of Search .......................................... 514/21, 12

[56] References Cited

PUBLICATIONS (Abstract) WO 92/09628, Immunodynamics, PCT Whole Document, Jun. 11, 1992.
(Abstract) EP 474506, Tomita et al., EP Whole Document, Mar. 11, 1992.
Halliwell "Drug Antioxidant Effects . . . ", Drugs (1991) V. 42 No. 4, pp. 569–605.
Rejman, " Bovine Lactoferrin . . . " (1989) (ABS Only) Medline AB #90:031466.

*Primary Examiner*—Cecilia J. Tsang
*Assistant Examiner*—Patrick R. Delaney
*Attorney, Agent, or Firm*—Wenderoth, Lind & Ponack, L.L.P.

[57] ABSTRACT

The present invention provides a safe antioxidant applicable for food, drug medicine, non-medical drug and other products.

The antioxidant of the present invention contains, as an effective ingredient, an antioxidant substance selected from the group consisting of a hydrolysate of lactoferrin, one or more peptides isolated from a hydrolysate of lactoferrins, one or more synthetic peptides having the same sequence as that of the peptide isolated from the hydrolysate of lactoferrins, and any mixture thereof, or said antioxidant substance and oxidant preventive agent.

This antioxidant has an excellent antioxidant action for various lipids, and is very safe even when used in foods and drug medicine. Scince it exhibits antioxidant effect with only small quantity, there is almost no adverse effect on flavor even when applied in foods and the like.

1 Claim, No Drawings

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa denotes any amino acid residue except Cys"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:1:

Lys Xaa Xaa Xaa Xaa Gln Xaa Xaa Met Lys Lys
1               5                   10

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa denotes any amino acid residue except Cys"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:2:

Lys Xaa Xaa Xaa Xaa Gln Xaa Xaa Met Arg Lys
1               5                   10

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="Xaa denotes any amino acid residue except Cys"

( i x ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

( x i ) SEQUENCE DESCRIPTION: SEQ ID NO:3:

Arg Xaa Xaa Xaa Xaa Arg
 1                5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa denotes any amino acid residue except Cys"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:4:

Lys Xaa Xaa Xaa Xaa Arg
 1                5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa denotes any amino acid residue except Cys"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:5:

Lys Xaa Xaa Xaa Xaa Lys (2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note="Xaa denotes any amino acid residue except Cys"

(ix) FEATURE:
        (A) NAME/KEY:
        (B) LOCATION:
        (C) IDENTIFICATION METHOD:
        (D) OTHER INFORMATION: /note="the specified peptide as well as peptides including the specified peptide as a fragment thereof"

(xi) SEQUENCE DESCRIPTION: SEQ ID NO:6:

Arg Xaa Xaa Xaa Xaa Lys
1                   5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note="Xaa denotes any amino acid residue except Cys"

(ix) FEATURE:
        (A) NAME/KEY:
        (B) LOCATION:
        (C) IDENTIFICATION METHOD:
        (D) OTHER INFORMATION: /note="the specified peptide as well as peptides including the specified peptide as a fragment thereof"

(xi) SEQUENCE DESCRIPTION: SEQ ID NO:7:

Arg Xaa Xaa Xaa Arg
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note="Xaa denotes any amino acid residue except Cys"

( i x ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

( x i ) SEQUENCE DESCRIPTION: SEQ ID NO:8:

```
Lys  Xaa  Xaa  Xaa  Arg
 1                    5
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="Xaa denotes any amino acid residue except Cys"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:9:

```
Arg  Xaa  Xaa  Xaa  Lys
 1                    5
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:10:

```
Phe  Gln  Trp  Gln  Arg  Asn
 1                    5
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

( x i ) SEQUENCE DESCRIPTION: SEQ ID NO:11:

Phe Gln Trp Gln Arg
1                  5

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:12:

Gln Trp Gln Arg
1

( 2 ) INFORMATION FOR SEQ ID NO:13:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:13:

Trp Gln Arg
1

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:14:

Arg Arg Trp Gln Trp
1               5

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:15:

Arg Arg Trp Gln
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:16:

Trp Gln Trp Arg
1

( 2 ) INFORMATION FOR SEQ ID NO:17:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:17:

Gln Trp Arg
1

( 2 ) INFORMATION FOR SEQ ID NO:18:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY:
  ( B ) LOCATION:
  ( C ) IDENTIFICATION METHOD:
  ( D ) OTHER INFORMATION: /note="the specified peptide as well as peptides including the specified peptide as a fragment thereof"

( x i ) SEQUENCE DESCRIPTION: SEQ ID NO:18:

Leu Arg Trp Gln Asn Asp
1               5

( 2 ) INFORMATION FOR SEQ ID NO:19:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY:
  ( B ) LOCATION:
  ( C ) IDENTIFICATION METHOD:
  ( D ) OTHER INFORMATION: /note="the specified peptide as well as peptides including the specified peptide as a fragment thereof"

( x i ) SEQUENCE DESCRIPTION: SEQ ID NO:19:

Leu Arg Trp Gln Asn
1               5

( 2 ) INFORMATION FOR SEQ ID NO:20:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY:
  ( B ) LOCATION:
  ( C ) IDENTIFICATION METHOD:
  ( D ) OTHER INFORMATION: /note="the specified peptide as well as peptides including the specified peptide as a fragment thereof"

( x i ) SEQUENCE DESCRIPTION: SEQ ID NO:20:

Leu Arg Trp Gln
1

( 2 ) INFORMATION FOR SEQ ID NO:21:

( i ) SEQUENCE CHARACTERISTICS:
  ( A ) LENGTH: 3 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
                   ( A ) NAME/KEY:
                   ( B ) LOCATION:
                   ( C ) IDENTIFICATION METHOD:
                   ( D ) OTHER INFORMATION: /note="the specified peptide as well
                         as peptides including the specified peptide as a fragment
                         thereof"

( x i ) SEQUENCE DESCRIPTION: SEQ ID NO:21:

Arg  Trp  Gln
 1

( 2 ) INFORMATION FOR SEQ ID NO:22:

( i ) SEQUENCE CHARACTERISTICS:
                   ( A ) LENGTH: 20 amino acids
                   ( B ) TYPE: amino acid
                   ( C ) STRANDEDNESS: single
                   ( D ) TOPOLOGY: linear ( i i ) MOLECULE TYPE: peptide ( i x ) FEATURE:
                   ( A ) NAME/KEY:
                   ( B ) LOCATION:
                   ( C ) IDENTIFICATION METHOD:
                   ( D ) OTHER INFORMATION: /note="the specified peptide as well
                         as peptides including the specified peptide as a fragment
                         thereof"

( i x ) FEATURE:
                   ( A ) NAME/KEY:
                   ( B ) LOCATION:
                   ( C ) IDENTIFICATION METHOD:
                   ( D ) OTHER INFORMATION: /note="cysteine residues at
                         positions 2 and 19 are bonded by disulfide linkage"

( x i ) SEQUENCE DESCRIPTION: SEQ ID NO:22:

Lys  Cys  Arg  Arg  Trp  Gln  Trp  Arg  Met  Lys  Lys  Leu  Gly  Ala
 1              5                            10

Pro  Ser  Ile  Thr  Cys  Val
15                    20

( 2 ) INFORMATION FOR SEQ ID NO:23:

( i ) SEQUENCE CHARACTERISTICS:
                   ( A ) LENGTH: 20 amino acids
                   ( B ) TYPE: amino acid
                   ( C ) STRANDEDNESS: single
                   ( D ) TOPOLOGY: linear ( i i ) MOLECULE TYPE: peptide ( i x ) FEATURE:
                   ( A ) NAME/KEY:
                   ( B ) LOCATION:
                   ( C ) IDENTIFICATION METHOD:
                   ( D ) OTHER INFORMATION: /note="the specified peptide as well
                         as peptides including the specified peptide as a fragment
                         thereof"

( i x ) FEATURE:
                   ( A ) NAME/KEY:
                   ( B ) LOCATION:
                   ( C ) IDENTIFICATION METHOD:
                   ( D ) OTHER INFORMATION: /note="cysteine residues at positions
                         2 and 19 are chemically modified to prevent disulfide
                         linkage"

( x i ) SEQUENCE DESCRIPTION: SEQ ID NO:23:

Lys  Cys  Arg  Arg  Trp  Gln  Trp  Arg  Met  Lys  Lys  Leu  Gly  Ala
 1              5                            10

Pro Ser Ile Thr Cys Val
15                  20

( 2 ) INFORMATION FOR SEQ ID NO:24:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="cysteine residues at positions 2 and 19 are bonded by disulfide linkage"

( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( x i ) SEQUENCE DESCRIPTION: SEQ ID NO:24:

Lys Cys Phe Gln Trp Gln Arg Asn Met Arg Lys Val Arg Gly
1               5                   10

Pro Pro Val Ser Cys Ile
15              20

( 2 ) INFORMATION FOR SEQ ID NO:25:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( C ) IDENTIFICATION METHOD:
        ( D ) OTHER INFORMATION: /note="the specified peptide as well as peptides including the specified peptide as a fragment thereof"

( i x ) FEATURE:
        ( A ) NAME/KEY:
        ( B ) LOCATION:
        ( C ) IDENTIFICATION METHOD:
        ( D ) OTHER INFORMATION: /note="cysteine residues at positions 2 and 19 are chemically modified to prevent disulfide linkage"

( x i ) SEQUENCE DESCRIPTION: SEQ ID NO:25:

Lys Cys Phe Gln Trp Gln Arg Asn Met Arg Lys Val Arg Gly
1               5                   10

Pro Pro Val Ser Cys Ile
15              20

( 2 ) INFORMATION FOR SEQ ID NO:26:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear (  i i  ) MOLECULE TYPE: peptide (  i x  ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

(  i x  ) FEATURE:
    ( A ) NAME/KEY:
    ( B ) LOCATION:
    ( C ) IDENTIFICATION METHOD:
    ( D ) OTHER INFORMATION: /note="cysteine residues at positions 3 and 20 are bonded by disulfide linkage"

( x i ) SEQUENCE DESCRIPTION: SEQ ID NO:26:

```
Phe  Lys  Cys  Arg  Arg  Trp  Gln  Trp  Arg  Met  Lys  Lys  Leu  Gly
1                  5                            10
Ala  Pro  Ser  Ile  Thr  Cys  Val  Arg  Arg  Ala  Phe
15                       20                       25
```

( 2 ) INFORMATION FOR SEQ ID NO:27:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear (  i i  ) MOLECULE TYPE: peptide (  i x  ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

(  i x  ) FEATURE:
    ( A ) NAME/KEY:
    ( B ) LOCATION:
    ( C ) IDENTIFICATION METHOD:
    ( D ) OTHER INFORMATION: /note="cysteine residues at positions 16 and 33 are bonded by disulfide linkage"

( x i ) SEQUENCE DESCRIPTION: SEQ ID NO:27:

```
Lys  Asn  Val  Arg  Trp  Cys  Thr  Ile  Ser  Gln  Pro  Glu  Trp  Phe  Lys
1                   5                       10                          15
Cys  Arg  Arg  Trp  Gln  Trp  Arg  Met  Lys  Lys  Leu  Gly  Ala  Pro  Ser
                    20                       25                         30
Ile  Thr  Cys  Val  Arg  Arg  Ala  Phe
                    35
```

( 2 ) INFORMATION FOR SEQ ID NO:28:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear (  i i  ) MOLECULE TYPE: peptide (  i x  ) FEATURE:
    ( A ) NAME/KEY:
    ( B ) LOCATION:
    ( C ) IDENTIFICATION METHOD:
    ( D ) OTHER INFORMATION: /note="the specified peptide as well as peptides including the specified peptide as a fragment thereof"

( i x ) FEATURE:
  ( A ) NAME/KEY:
  ( B ) LOCATION:
  ( C ) IDENTIFICATION METHOD:
  ( D ) OTHER INFORMATION: /note="cysteine residues at positions
    10 and 27 are bonded by disulfide linkage"

( x i ) SEQUENCE DESCRIPTION: SEQ ID NO:28:

| Thr | Ile | Ser | Gln | Pro | Glu | Trp | Phe | Lys | Cys | Arg | Arg | Trp | Gln | Trp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Arg | Met | Lys | Lys | Leu | Gly | Ala | Pro | Ser | Ile | Thr | Cys | Val | Arg | Arg |
|-----|-----|-----|-----|-----|-----|-----|-----|-----|-----|-----|-----|-----|-----|-----|
|     |     |     |     | 20  |     |     |     |     | 25  |     |     |     |     | 30  |

| Ala | Phe |
|-----|-----|

( 2 ) INFORMATION FOR SEQ ID NO:29:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="the specified peptide as well
      as peptides including the specified peptide as a fragment
      thereof"

( i x ) FEATURE:
    ( A ) NAME/KEY:
    ( B ) LOCATION:
    ( C ) IDENTIFICATION METHOD:
    ( D ) OTHER INFORMATION: /note="cysteine residues at positions
      9 and 26 are linked by disulfide linkage"

( i x ) FEATURE:
    ( A ) NAME/KEY:
    ( B ) LOCATION:
    ( C ) IDENTIFICATION METHOD:
    ( D ) OTHER INFORMATION: /note="cysteine residues at position
      35 is linked by disulfide linkage with the cysteine
      residue at position 10 of SEQ ID No. 32"

( x i ) SEQUENCE DESCRIPTION: SEQ ID NO:29:

| Val | Ser | Gln | Pro | Glu | Ala | Thr | Lys | Cys | Phe | Gln | Trp | Gln | Arg | Asn |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Met | Arg | Lys | Val | Arg | Gly | Pro | Pro | Val | Ser | Cys | Ile | Lys | Arg | Asp |
|-----|-----|-----|-----|-----|-----|-----|-----|-----|-----|-----|-----|-----|-----|-----|
|     |     |     |     | 20  |     |     |     |     | 25  |     |     |     |     | 30  |

| Ser | Pro | Ile | Gln | Cys | Ile |
|-----|-----|-----|-----|-----|-----|
|     |     |     |     | 35  |     |

( 2 ) INFORMATION FOR SEQ ID NO:30:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY:
    ( B ) LOCATION:
    ( C ) IDENTIFICATION METHOD:
    ( D ) OTHER INFORMATION: /note="Xaa denotes any amino acid residue except Cys"

(ix) FEATURE:
 (A) NAME/KEY:
 (B) LOCATION:
 (C) IDENTIFICATION METHOD:
 (D) OTHER INFORMATION: /note="the specified peptide as well as peptides including the specified peptide as a fragment thereof"

(xi) SEQUENCE DESCRIPTION: SEQ ID NO:30:

```
Lys  Xaa  Xaa  Xaa  Lys
 1                    5
```

(2) INFORMATION FOR SEQ ID NO:31:

(i) SEQUENCE CHARACTERISTICS:
  (A) LENGTH: 11 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY:
  (B) LOCATION:
  (C) IDENTIFICATION METHOD:
  (D) OTHER INFORMATION: /note="the specified peptide as well as peptides including the specified peptide as a fragment thereof"

(xi) SEQUENCE DESCRIPTION: SEQ ID NO:31:

```
Lys  Thr  Arg  Arg  Trp  Gln  Trp  Arg  Met  Lys  Lys
 1                    5                   10
```

(2) INFORMATION FOR SEQ ID NO:32:

(i) SEQUENCE CHARACTERISTICS:
  (A) LENGTH: 11 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY:
  (B) LOCATION:
  (C) IDENTIFICATION METHOD:
  (D) OTHER INFORMATION: /note="the specified peptide as well as peptides including the specified peptide as a fragment thereof"

(ix) FEATURE:
  (A) NAME/KEY:
  (B) LOCATION:
  (C) IDENTIFICATION METHOD:
  (D) OTHER INFORMATION: /note="cysteine residues at position 10 is linked by disulfide linkage with the cysteine residue at position 35 of SEQ ID No. 29"

(xi) SEQUENCE DESCRIPTION: SEQ ID NO:32:

```
Gly  Arg  Arg  Arg  Arg  Ser  Val  Gln  Trp  Cys  Ala
 1                    5                   10
```

ANTIOXIDANT

TECHNICAL FIELD

The present invention relates to an antioxidant. More particularly, the present invention relates to a safe antioxidant applicable for food, drug medicine, non-medical drug and other products.

BACKGROUND ART

Oils and fats are oxidized by oxygen contained in the atmosphere, thus producing peroxides. Peroxides are relatively unstable and further produce carbonyl and other compounds through polymerization and decomposition. These carbonyl and other compounds form major ingredients causing bad odor.

Peroxides and other compounds such as carbonyl cause deterioration of flavor and degradation of quality of oils and fats, and in addition, these peroxides, when absorbed, exert detrimental effects in vivo. In an experiment in which a large dose of a lipid peroxide was administered to animals during a short period of time, peroxide have been clarified to induce troubles in the liver function and the immune system.

Oxidation reactions in vivo are known to relate to aging and various diseases. More specifically, active oxygen produced in vivo oxidizes lipid rich in unsaturated fatty acid, causes progress of radical linkage peroxidizing reaction, and produces peroxidized lipid such as lipid hydroperoxide. Decomposition of lipid hydroperoxide produces active oxygen species such as highly reactive alkoxy radical, peroxy radical, and singlet oxygen, thus causing progress of linkage reactions.

Free radicals and active oxygen species generated in the course of oxidation reaction denature protein in vivo, inactivate enzymes, bring about mutation in DNA, and finally cause various diseases including aging and cancer.

Many substances are known to have antioxidant action, including for example certain amino acids [Marcuse, R.: Nature, Vol. 188, p. 866, 1960], protein having a metal chelating function (Kajimoto and Yoshida: Yukagaku, Vol. 21, p. 200, 1972), dipeptide (Yamaguchi, et al.: Journal of the Japan Food Industry Association, Vol. 22, p. 425, 1975), and a certain peptide available by enzymatic decomposition of egg albumin (Tsuge, et al.: Journal of the Agricultural Chemical Society of Lapan, Vol. 65, p. 1635, 1991).

Regarding lactoferrins which are natural iron-binding proteins contained in lacrima, saliva, peripheral blood, and milk of mammals, there is known the inhibiting effect of generation of iron-dependent peroxidized lipid [Gutteridge, J. M. C., et al.: Biochemical Journal, Vol.199, p.259, 1981], and an anti-aging food product based on blending of lactoferrin is proposed (Japanese Patent Provisional Publication No. 4-58,871).

However, the antioxidant action of a hydrolysate of lactoferrins or of a peptide in such a hydrolysate has not as yet been known at all, and there has been present no antioxidant containing them as an effective ingredient.

DISCLOSURE OF INVENTION

The present invention has an object to provide a safe antioxidant containing, unlike the conventional antioxidants, a hydrolysate of lactoferrins, and/or peptide in the hydrolysate as effective ingredients.

The present invention provides an antioxidant, of which an effective ingredient is an antioxidant substance selected from the group consisting of a hydrolysate of lactoferrins, one or more peptides isolated from a hydrolysate of lactoferrins, one or more synthetic peptides having the same amino acid sequence as that of the peptide isolated from the hydrolysate of lactoferrins, and any mixture thereof.

The present invention provides also an antioxidant containing, as effective ingredients, an oxidation preventive agent and an antioxidant substance selected from the group consisting of a hydrolysate of lactoferrins, one or more peptides isolated from a hydrolysate of lactoferrins, one or more synthetic peptides having the same amino acid sequence as that of the peptide isolated from the hydrolysate of lactoferrins, and any mixture thereof.

This antioxidant has an excellent antioxidant action for various lipids, and is very safe even when used in foods and drug medicine. Since it exhibits antioxidant effect with only a small quantity, there is almost no adverse effect on flavor even when applied in foods.

BEST MODE FOR CARRYING OUT THE INVENTION

In the present invention, lactoferrins used as the starting material include: commercially available lactoferrins; lactoferrins isolated from mammalian milk such as colostrum, transitional milk, normal milk, late lactation milk, and the like and processed products thereof such as skim milk and whey; apolactoferrin obtainable by de-ironization thereof with an inorganic or organic acid; metal-saturated and partially metal-saturated lactoferrins obtainable by chelation of the above-mentioned apo-lactoferrins with a metal such as iron, copper, zinc, manganese and the like, and a commercially available product or one prepared by a conventional method or a mixture thereof may be used.

The lactoferrin hydrolysate used in the present invention is obtainable by the method disclosed, for example in Japanese Patent Application No. 3-171,736 comprising the step of hydrolyzing the above-mentioned lactoferrin with an acid or protease. More specifically, hydrolysis with an acid is carried out by making an aqueous solution of lactoferrin, adding an inorganic or organic acid, and heating the mixture to a prescribed temperature for a prescribed period of time. Hydrolysis with a protease is conducted by making an aqueous solution of lactoferrin, adjusting pH thereof to a value optimum for the protease used, adding a protease such as pepsin or trypsin, and holding the mixture at a prescribed temperature for a prescribed period of time. After hydrolysis, the protease is deactivated by the conventional method. The thus lactoferrin hydrolysate is a mixture of decomposition products containing peptides and having various molecular weights. The degree of decomposition achieved in the hydrolysis described above should preferably be within a range of from 6 to 20%. The degree of decomposition is determined by measuring the total nitrogen content of the sample by the Kjeldahl method, and the formol nitrogen of the sample by the formol titration method, and calculating the following formula with the resultant values:

Degree of decomposition=(formol nitrogen/total nitrogen)×100

The reaction solution (solution of lactoferrin hydrolysates) obtained through hydrolysis as described above is cooled by the conventional method, and as required, neutralized, desalted or decolorized, followed as required by fractionation. The resultant solution is in the form of concentrated liquid, or in the form of powder dried after concentration.

Peptide used in the present invention can be obtained by any of the methods disclosed, for example, in Japanese Patent Provisional Publications Nos. 5-92,994, 5-78,392, 5-148,295, 5-148,296, and 5-148,297, i.e., the method comprising hydrolyzing a lactoferrin with an acid or a protease and obtaining a fraction containing a peptide from the decomposition mixture by a separating means such as liquid chromatography; or the method comprising determining the amino acid sequence of the peptide obtained as described above by a known method (e.g., the method using a gas-phase sequencer), and obtaining the target peptide by synthesizing peptides containing the peptide of the above-mentioned amino acid sequence by a known method (e.g., the method using an automatic peptide synthesizer). Furthermore, peptide solution may be obtained by concentrating as required a fraction containing peptide separated from the lactoferrin hydrolysate or a solution containing peptide derived from organic synthesis, and powdery peptide may be obtained by concentrating and drying this liquid product by any conventional method.

From among peptides capable of being prepared by the above-mentioned methods, preferable peptides isolated from lactoferrins include one or more of peptides of sequence numbers 1 to 30 and 32. Preferable synthesized peptides having the same amino acid sequence as that of the peptides isolated from lactoferrins include one or more of peptides of sequence numbers 1 to 32.

In the following description, peptides to be isolated from lactoferrins and synthetic peptides having the same amino acid sequence as that of the above, including the peptides of sequence numbers of from 1 to 32, may be collectively referred to as "peptides."

The antioxidant of the present invention, whether it is a hydrolysate of lactoferrin, any of peptides or a mixture thereof, has an excellent antioxidant action.

In addition, the antioxidant of the present invention exhibits a stronger antioxidant action by combining any of the above-mentioned hydrolysate of lactoferrins, peptides or mixture thereof with an oxidation preventive agent. It is possible to use any of a compound selected from the group consisting of vitamin E (tocopherol), vitamin C (ascorbic acid), vitamin A,β-carotene, superoxide dismutase, coenzyme Q, and a mixture of any of the above.

What of the above-mentioned oxidation preventive agents is to be combined with any of hydrolysate of lactoferrins, peptides or a mixture thereof may be appropriately determined according to the purpose of use. An appropriate mixing ratio of these ingredients may be selected taking account of the kinds of ingredients and the purpose of use. These ingredients may be mixed in liquid or powdery state, and the mixture may be added with an appropriate known diluent or excipient.

Now, the functions and effects of the present invention is described below with reference to Tests.

Test 1

This test was carried out to investigate antioxidant function of various antioxidant substances and compounds.

1) Preparation of samples:

A sample was prepared by adding dl-α tocopherol (manufactured by Wako Jun-yaku Kogyo Company), bovine lactoferrin (manufactured by Sigma Company), hydrolysate of lactoferrin (prepared by the same method as in the Example 2), or peptide (prepared by the same method as in the Example 3) to a final concentration of 0.2% (weight percentage; same applies hereafter except for the degree of decomposition) to commercially available linoleic acid (manufactured by Wako Jun-Yaku Kogyo Company) containing no additive. Hereafter, the thus prepared samples are individually referred to as Samples 2, 3, 4, 5 and 1.

2) Procedure:

Antioxidant effect of the individual samples was tested by the method of Mitsuda et al.(Eiyo to Shokuryo, Vol. 19, p. 210, 1966) described below.

The above-mentioned samples were added to a mixed solution containing 10 ml of ethanol, 10 ml of 0.1M phosphate buffer solution (pH: 7.0), and 5 ml of deionized water so as to achieve a final concentration of linoleic acid of $2\times10^2 M$(mol/l). This solution was placed in a vial bottle having a capacity of 50 ml, and the closely plugged bottle was held in an incubator at 60° C. The total volume was always adjusted to 25 ml by reducing the above-mentioned ionized water, depending upon the quantity of added sample. At prescribed time intervals, 0.1 ml was sampled from this vial bottle to measure the quantity of peroxides by the following ferric thiocyanate method.

To the sample solution in an amount of 0.1 ml, 4.7 ml of 75% ethanol, 0.1 ml of 30% ammonium rhodanide, and 0.1 ml of 3.5% hydrochloric acid solution of $2\times10^{-2}M$ ferrous chloride were added, and absorbance at 500 nm was measured upon the lapse of just three minutes.

3) Results:

The results of this test are as shown in Table 1. As is clear from Table 1, oxidation of linoleic acid was prevented in the Sample 4 (single addition of hydrolysate of lactoferrin) more remarkably and the Sample 5 (single addition of peptides) than in the sample 3 (single addition of lactoferrin) and the Sample 2 (single addition of dl-α tocopherol). Tests were carried out also for hydrolysate of lactoferrins and peptides other than those mentioned above, and similar linoleic acid oxidation preventing effect was observed.

TABLE 1

| Period of preservation (days) | Degree of peroxidation (absorbance at 500 nm) | | | | |
| --- | --- | --- | --- | --- | --- |
| | Sample 1 | Sample 2 | Sample 3 | Sample 4 | Sample 5 |
| 0 | 0 | 0 | 0 | 0 | 0 |
| 3 | 0.22 | 0.19 | 0.23 | 0.13 | 0.05 |
| 6 | 1.66 | 0.16 | 0.30 | 0.15 | 0.07 |
| 10 | 1.85 | 0.16 | 0.31 | 0.18 | 0.11 |
| 13 | 1.53 | 0.21 | 0.32 | 0.16 | 0.10 |

The following 11 kinds of sample were prepared.

Sample 1: Linoleic acid with no additive (the same sample as in the Test 1);

Sample 2: A sample prepared by adding a hydrolysate of lactoferrin (prepared by the same method as in the Example 2) to linoleic acid to achieve a final concentration of 0.1%;

Sample 3: A sample prepared by adding peptides (prepared by the same method as in the Example 3) to linoleic acid to achieve a final concentration of 0.1%;

Sample 4: A sample prepared by adding vitamin E (dl-α tocopherol the same one as in the Test 1) to linoleic acid to achieve a final concentration of 0.1%;

Sample 5: A sample prepared by adding superoxide dismutase (manufactured by Sigma Company) to linoleic acid to achieve a final concentration of 0.1%;

Sample 6: A sample prepared by adding β-carotene (manufactured by Nakaraitesk Company) to linoleic acid to achieve a final concentration of 0.1%;

Sample 7: A sample prepared by adding vitamin C (manufactured by Nakaraitesk Company) to linoleic acid to achieve a final concentration of 0.1%;

Sample 8: A sample prepared by adding a hydrolysate of lactoferrin (prepared by the same method as in the Example 2) to achieve a final concentration of 0.01% and vitamin E to achieve a final concentration of 0.01% to linoleic acid;

Sample 9: A sample prepared by adding a hydrolysate of lactoferrin (prepared by the same method as in the Example 2) to achieve a final concentration of 0.01% and superoxide dismutase to achieve a final concentration of 0.01% to linoleic acid;

Sample 10: A sample prepared by adding peptide (prepared by the same method as in the Example 3) to achieve a final concentration of 0.01% and β-carotene to achieve a final concentration of 0.01% to linoleic acid;

Sample 11: A sample prepared by adding peptide (prepared by the same method as in the Example 3) to achieve a final concentration of 0.01% and vitamin C to achieve a final concentration of 0.01% to linoleic acid.

2) Procedure:

Absorbance was measured by the same method as in the Test 1, and with the number of days until an absorbance of 0.2 is exceeded as the inducing period, antioxidant effect was tested.

3) Results:

The results of this test are as shown in Table 2. As is clear from Table 2, the inducing period for the Sample 8 (added with a hydrolysate of lactoferrin and vitamin E), the Sample 9 (added with a hydrolysate of lactoferrin and superoxide dismutase), the Sample 10 (added with peptide and β-carotene), and the Sample 11 (added with peptide and vitamin C) increased remarkably, showing a very strong antioxidant effect to linoleic acid. Similar results were obtained also for combinations of hydrolysates of lactoferrin or peptides other than those mentioned above and oxidation preventive agents other than those described above.

TABLE 2

| Sample No. | Sample substances added | Inducing period (days) |
|---|---|---|
| 1 | No addition (control) | 2 |
| 2 | Hydrolysate of lactoferrin | 14 |
| 3 | Peptide isolated from hydrolysate of lactoferrin | 20 |
| 4 | Vitamin E | 8 |
| 5 | Superoxide dismutase | 10 |
| 6 | β-carotene | 14 |
| 7 | Vitamin C | 8 |
| 8 | Hydrolysate of lactoferrin + vitamin E | 30 |
| 9 | Hydrolysate of lactoferrin + superoxide dismutase | >40 |
| 10 | Peptide isolated from hydrolysate of lactoferrin + β-carotene | >40 |
| 11 | Peptide isolated from hydrolysate of lactoferrin + vitamin C | 35 |

EXAMPLES

Now, the present invention is described below further in detail and concretely by means of Examples. The present invention is not limited to these Examples. The commercially available oxidation preventive agent used in the following Examples is the same as that used in the Tests.

Example 1

About 1,000 g of a solution of lactoferrin hydrolysate was yielded in such a manner that: 50 g of commercially available lactoferrin just as isolated from cow's milk was dissolved into 950 g of distilled water: the resultant solution was heated at 120° C. for 15 minutes after the pH of the resultant solution was adjusted to 2 with 1N hydrochloric acid; then, the resultant solution of lactoferrin hydrolysate was cooled (concentration of the lactoferrin hydrolysate: 5%). The hydrolyzing rate of the product was 9%.

From the solution of lactoferrin hydrolysate, about 49 g of powdery antioxidant was yielded by concentrating the solution under a reduced pressure, followed by freezedrying.

Example 2

About 10 kg of a solution of lactoferrin hydrolysate (concentration of the products: 10%) was yielded in such a manner that 1 kg of commercially available lactoferrin (manufactured by Oleofina Company, Belgium) just as isolated from cow's milk was dissolved into 9 kg of distilled water, followed by adjustment of pH to 2.5 by addition of 2M(mol/l) citric acid, addition of 30 g of commercially available swine pepsin (1:10000; manufactured by Wako Jun-yaku Co., Ltd.) to the resultant liquid, incubation of the resultant liquid at 37° C. for 180 minutes, deactivation of the pepsin by heating at 80° C. for ten minutes, and cooling the resultant solution. The hydrolyzing rate of the product was 11.3%.

From the solution of lactoferrin hydrolysate, about 960 g of powdery antioxidant was yielded by concentrating the solution under a reduced pressure, followed by freezedrying.

Example 3

Hydrolysis of lactoferrin was conducted in such a manner that: 50 mg of commercially available bovine lactoferrin (made by Sigma Company) was dissolved into 0.9 ml of distilled water; pH of the resultant solution was adjusted to 2.5 by addition of 0.1N hydrochloric acid; after adding 1 mg of commercially available swine pepsin (made by Sigma Company) the resultant solution was hydrolyzed at 37° C. for six hours; the pH of the resultant solution was adjusted to 7.0 with 0.1N sodium hydroxide; then the enzyme was deactivated by heating at 80° C. for ten minutes; the resultant liquid was cooled to the room temperature and centrifuged at 15,000 rpm for 30 minutes, thereby obtaining a clear supernatant containing lactoferrin hydrolysate. Then, 100 μl of the supernatant was subjected to high performance liquid chromatography by passing same through a column of TSK gel ODS-120T (manufactured by Toso Company) at a flow rate of 0.8 ml/min., then the column was rinsed with 20% of acetonitrile containing 0.05% of TFA (trifluoroacetic acid) for ten minutes. Acetonitrile gradient (20–60%) containing 0.05% of TFA was further passed through the column for 30 minutes during which period a fraction eluted between 24–25 minutes was collected and dried under a reduced pressure. The resultant powder was dissolved into distilled water to make a 2% (w/v) solution which was subjected to high performance liquid chromatography by passing same through a column of TSK gel ODS-120T (made by Toso Company) at a flow rate of 0.8 ml/min. Acetonitrile (24%) containing 0.05% TFA was passed through the column for ten minutes, then 24–32% acetonitrile gradient containing 0.05% of TFA was passed through the column for 30 minutes during which a fraction eluted between 33.5–35.5 minutes was collected. The latter HPLC processing was repeated 25 times, and the resultant eluate was dried under a reduced pressure to thereby obtain 1.5 mg of antioxidant comprising a powdery peptide separated from the hydrolysate of bovine lactoferrin.

The obtained peptide was hydrolyzed with 6N hydrochloric acid, then amino acid composition thereof was analyzed with an amino acid analyzer in accordance with the conventional method. The same sample was subjected to gas phase sequencer (manufactured by Applied Biosystems Company) to gave Edman degradation 25 times, whereby the sequence of 25 amino acid residues was determined. Also, presence of disulfide linkage in the peptide was confirmed by the disulfide-linkage analysis (Analytical Biochemistry, Vol. 67, page 493, 1975) utilizing DTNB (5,5-dithio-bis(2-nitrobenzoic acid)).

As a result, it was confirmed that this peptide had an amino acid sequence as shown in Sequence No. 26 (infra), consisting of 25 amino acid residues, and having a disulfide linkage between the third and the twentieth cysteine residues, and that two amino acid residues bonded to the third cysteine residue on the N-terminus side, and five amino acid residues bonded to the twentieth cysteine residue on the C-terminus side.

Example 4

Synthesis of a peptide of the sequence No.31 was conducted with peptide synthesizer (LKB Bioynx 4170, manufactured by Pharmacia LKB Biotechnology Company) in accordance with Solid Phase Peptide Synthesis by Sheppard et al. (Journal of Chemical Society Perkin I., page 538, 1981), the particulars of which are as follows:

Anhydrides of desired amino acids were produced by adding N,N-dicyclohexylcarbodiimide to said amino acids of which amine-functional groups were previously protected with 9-fluorenyl methoxy carbonyl groups. The resultant Fmoc-amino acid anhydrides were used for synthesis of the peptide. Peptide chains in a known amino acid sequence were formed in such a manner that Fmoc-lysine anhydrides which correspond to the lysine residue at the C-terminus of the peptide was fixed to ultrosyn A resin (manufacturedby Pharmacia LKB Biotechnology Company) with their carboxyl groups in the presence of dimethylaminopyridine as a catalyst. Washing the resin with dimethylformamide containing pyperidine to thereby remove the protective groups bonded to amine-functional groups of the C-terminus amino acids (lysine); the Fmoc-lysine anhydrides which correspond to 2nd amino acid from the C-terminus in the amino acid sequence were coupled to the deprotected amine-functional groups of the C-terminus lysine which was previously fixed to the resin. In the same manner, methionine, arginine, tryptophan, glutamine, tryptophan, arginine, arginine, threonine, and lysine were successively coupled to the amino acid which was coupled immediately before. When the successive coupling of all amino acids was completed, and the aimed peptide chains having the desired sequence were formed, removal of the protective groups other than acetamid-methyl and detachment of the synthesized peptides from the resin were performed by addition of a solvent consisting of 94% TFA, 5% of phenol, and 1% of ethandiol, the resultant solution of the peptide was purified with HPLC, then the purified solution was concentrated and dried to thereby obtain an antioxidant comprising a powdery synthetic peptide.

The resultant peptide was analyzed in the same manner as in the Example 3, thereby confirming that the synthesized peptide has the amino acid sequence of Sequence No. 31.

Example 5

Tablets of the following composition were prepared by a conventional method:

| Lactose | 79.45(%) |
| Ascorbic acid | 0.30 |
| dl-α tocopherol | 0.10 |
| Antioxidant of Example 4 | 0.15 |
| Magnesium stearate | 20.00 |

Example 6

An injection drug of the following composition was manufactured by a conventional method:

| Antioxidant of Example 3 | 1.20(%) |
| Surfactant | 8.00 |
| Physiological saline | 90.80 |

Example 7

A chewing gum of the following composition was manufactured by a conventional method:

| β-carotene | 0.50(%) |
| Gum base | 25.00 |
| Calcium carbonate | 2.00 |
| Aromatic | 1.00 |
| Antioxidant of Example 2 | 1.10 |
| Sorbitol powder | 70.40 |

Example 8

A hand lotion of the following composition was manufactured by a conventional method:

| Carbo-wax | 9.00(%) |
| Alcohol | 4.00 |
| Propylene glycol | 47.00 |
| Superoxide dismutase | 0.20 |
| Aromatic | 0.50 |
| Antioxidant of Example 1 | 0.40 |
| Distilled water | 38.90 |

Industrial Applicability

The antioxidant of the present invention is applicable not only as a medical drug, but also may be used by blending into products to be ingested or applied onto the body surface of human being or an animal such as foods, feedstuff, and cosmetics, and all products which should preferably inhibit peroxidation of lipid in general, and furthermore, it is possible to treat such products or raw materials with the antioxidant of the present invention. More specifically, the antioxidant of the present invention can be administered to a person or an animal as it is, or may be added, blended, sprayed, adhered, used to cover or impregnation of such products as foods (e.g. modified milk, chewing gum), drug medicine (e.g. oxidation inhibiting agent), non-medical drugs (eg.health-keeping agent), various cosmetics (e.g, hair liquid, cream, emulsion), raw materials thereof, and other materials which should preferably inhibit peroxidation of lipid in general.

We claim:

1. An antioxidant which contains an oxidation preventive agent selected from the group consisting of vitamin E (tocopherol), vitamin C (ascorbic acid), vitamin A, β-carotene, superoxide dismutase, coenzyme Q, and any mixture thereof, and an antioxidant substance selected from the group consisting of a hydrolysate of lactoferrins having a degree of decomposition of from 6 to 20, and SEQ ID NO:26, and any mixture thereof as effective components.

* * * * *